United States Patent
Grunhut

(10) Patent No.: US 9,452,263 B2
(45) Date of Patent: Sep. 27, 2016

(54) PLUNGER ROD WITH DOSE SETTING MEANS AND INJECTION DEVICE

(75) Inventor: Guillaume Grunhut, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 204 days.

(21) Appl. No.: 14/344,656

(22) PCT Filed: Sep. 14, 2012

(86) PCT No.: PCT/EP2012/068059
§ 371 (c)(1),
(2), (4) Date: Mar. 13, 2014

(87) PCT Pub. No.: WO2013/037937
PCT Pub. Date: Mar. 21, 2013

(65) Prior Publication Data
US 2014/0343511 A1    Nov. 20, 2014

(30) Foreign Application Priority Data

Sep. 16, 2011 (EP) .................................... 11306165

(51) Int. Cl.
*A61M 5/315* (2006.01)

(52) U.S. Cl.
CPC ....... *A61M 5/31501* (2013.01); *A61M 5/3156* (2013.01); *A61M 5/31515* (2013.01); *A61M 5/31555* (2013.01); *A61M 5/31578* (2013.01); *A61M 5/31593* (2013.01); *A61M 2005/31506* (2013.01); *A61M 2005/31508* (2013.01); *A61M 2005/31518* (2013.01)

(58) Field of Classification Search
CPC ........... A61M 5/315; A61M 5/31501; A61M 5/31515; A61M 5/31555; A61M 5/3156; A61M 5/31578; A61M 2005/31518
See application file for complete search history.

(56) References Cited

U.S. PATENT DOCUMENTS

| | | |
|---|---|---|
| 1,718,602 A | 6/1929 | Smith |
| 2,739,591 A | 3/1956 | Yochem |
| 2,869,543 A | 1/1959 | Ratcliff et al. |
| 3,370,754 A | 2/1968 | Cook et al. |
| 3,477,432 A | 11/1969 | Shaw |
| 3,680,558 A | 8/1972 | Kapelowitz |
| 3,835,835 A | 9/1974 | Thompson et al. |

(Continued)

FOREIGN PATENT DOCUMENTS

| | | |
|---|---|---|
| WO | 03/020347 A2 | 3/2003 |
| WO | 2009/108847 A1 | 9/2009 |

(Continued)

*Primary Examiner* — Andrew Gilbert
(74) *Attorney, Agent, or Firm* — The Webb Law Firm

(57) ABSTRACT

The present invention relates to a plunger rod for an injection device, having a distal element slidingly coupled to a proximal element having at least one radially flexible branch. The plunger rod includes a lock for selectively locking the distal element and the proximal element in a plurality of relative axial positions defining a plurality of intermediate positions of the plunger rod, wherein the lock is movable from a locked state, in which the distal element and the proximal element are fixed with respect to each other in the axial direction, and an unlocked state, in which the distal element and the proximal element are displaceable in the axial direction with respect to each other, when the at least one radially flexible branch is displaced radially. The invention also relates to an injection device having such a plunger rod.

14 Claims, 4 Drawing Sheets

(56) References Cited

U.S. PATENT DOCUMENTS

| | | | |
|---|---|---|---|
| 4,171,698 A | 10/1979 | Genese | |
| 4,444,335 A * | 4/1984 | Wood | A61M 3/00 222/309 |
| 4,915,695 A * | 4/1990 | Koobs | A61M 5/315 222/137 |
| 5,009,645 A * | 4/1991 | Silver | A61M 5/31555 604/207 |
| 5,468,232 A * | 11/1995 | Naganuma | A61M 5/24 604/200 |
| 9,101,719 B2 * | 8/2015 | Vernizeau | A61M 5/002 |
| 2004/0015120 A1 * | 1/2004 | Berman | A61M 31/00 604/11 |
| 2007/0244444 A1 * | 10/2007 | Guelker | A61D 7/00 604/207 |
| 2009/0318880 A1 * | 12/2009 | Janish | A61M 5/31511 604/228 |
| 2009/0326479 A1 * | 12/2009 | Janish | A61M 5/31511 604/218 |
| 2011/0049181 A1 * | 3/2011 | Lutz | A61J 1/2096 222/137 |
| 2011/0222366 A1 * | 9/2011 | Axen | A61B 17/8825 366/176.3 |
| 2013/0126559 A1 * | 5/2013 | Cowan | A61M 5/31525 222/333 |
| 2013/0253435 A1 * | 9/2013 | Vernizeau | A61M 5/002 604/192 |

FOREIGN PATENT DOCUMENTS

| | | |
|---|---|---|
| WO | 2009/108869 A1 | 9/2009 |
| WO | 2010/072702 A1 | 7/2010 |

* cited by examiner

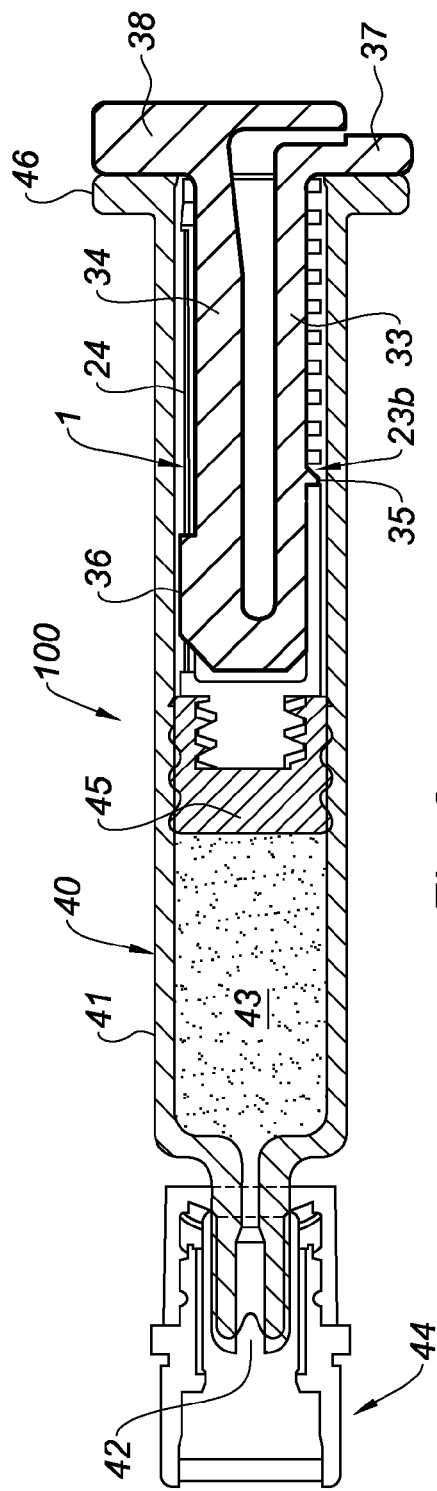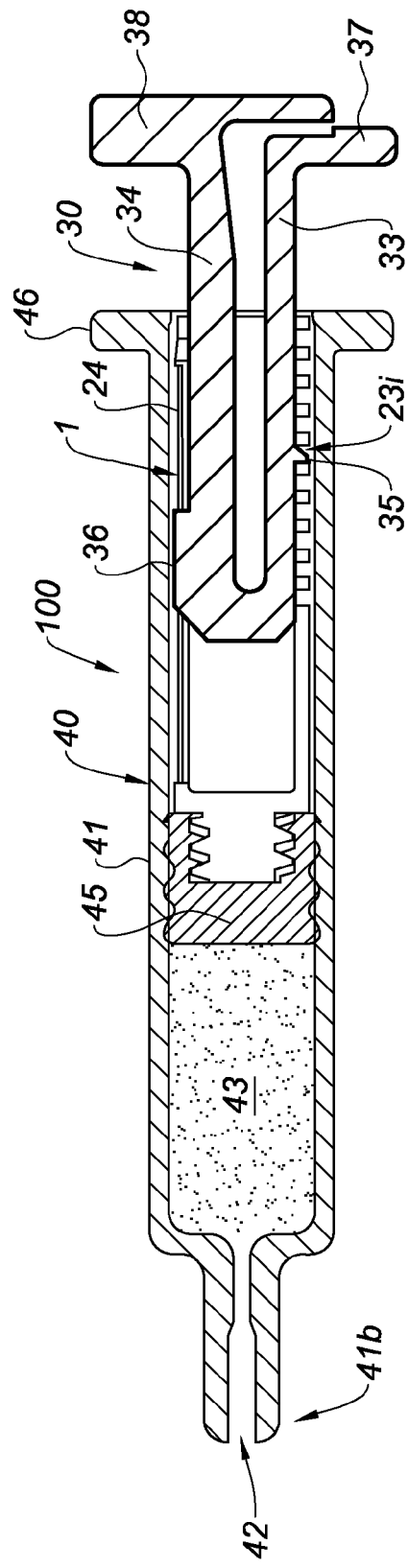

PLUNGER ROD WITH DOSE SETTING MEANS AND INJECTION DEVICE

CROSS-REFERENCE TO RELATED APPLICATIONS

This application is the United States national phase of International Application No. PCT/EP2012/068059 filed Sep. 14, 2012, and claims priority to European Patent Application No. 11306165.9 filed Sep. 16, 2011, the disclosures of which are hereby incorporated in their entirety by reference.

BACKGROUND OF THE INVENTION

1. Field of the Invention

The present invention relates to a plunger rod for an injection device, said plunger rod allowing the delivery of selected doses of product while being very compact. The invention further relates to a compact injection device comprising such a plunger rod.

2. Description of Related Art

In this application, the distal end of an element or of a device means the end furthest away from the hand of the user and the proximal end means the end closest to the hand of the user, when the element or device is in the use-position. Similarly, in this application, the terms "in the distal direction" and "distally" mean in the direction of the injection, and the terms "in the proximal direction" and "proximally" mean in the direction opposite to the direction of injection.

Injection devices, such as syringes, are well known. Many different types of injection devices have been designed for administering medicines. Injection devices usually comprise a container intended to receive the product to be injected and a plunger rod intended to move a stopper within the container so as to expel the product therefrom at the time of injection. Empty and pre-filled disposable injection devices exist but prefilled devices are now preferred because they are more convenient, safe and efficient and may be used directly in emergency cases.

In some cases, the administration of a medicine requires the injection of a very specific dose of product. In other cases, the injection step may be divided into several successive steps, as for example where several doses of the product are to be injected one after the other. In addition, the successive doses of product to be injected may have different volumes.

The administration of certain particular medicinal products also may require a succession of precise steps. Thus, in the case of anti-cancer products for example, the active principle must be stored separately from the solvent with which it should only be mixed just before the time of injection. Injection devices such as syringes provided with two separate chambers, one containing the active principle and the other its solvent, are used for this purpose. In such cases, the plunger rod is displaced along a first distance, whereupon the active principle is transferred along a by-pass system and enters in the chamber containing the solvent. Once the medicine is reconstituted, the plunger rod is displaced along a second distance for completing the injection step as such. This step may itself be divided into several steps to inject several doses as already described.

In all the cases mentioned above, it is particularly important that the plunger rod be stopped exactly and precisely right after being displaced along a certain distance, and for a repeated number of times if necessary.

Moreover, prefilled injections devices are usually filled by a pharmaceutical company, packaged for use, and then typically stored at a doctor's office, hospital, etc. until they are needed for use. In such a condition, the prefilled injection device will take up a predetermined amount of storage space based upon the size of the injection device (typically including a syringe barrel, a stopper, a plunger rod, and possibly a needle). In some cases, the predetermined amount of storage space the injection device will take up is a maximum space approximating the length of the plunger rod, plus the length of the syringe barrel, plus the length of the needle (if provided).

Required storage space is an important feature for prefilled injection devices. It is especially important when the medicine contained in these devices must be stored and transported at low temperatures. Storage of these injection devices may require refrigeration and can be expensive. This is especially the case in hospitals and pharmacies, where storage space for medicines is limited.

Thus, there is a need for an injection device which would be particularly compact, especially when the injection device is prefilled, and that would ensure the possibility of delivering specific selected doses of product, in a successive manner or not. There is therefore still a need for a safe and compact injection device which would avoid at least temporarily any inadvertent movement of the plunger rod past a predetermined limit, this injection device nevertheless allowing a subsequent movement of said plunger rod for at least one or more subsequent steps, and in particular for the delivery of one or several additional selected doses of product.

Moreover, such an injection device must be simple to use, and preferably would not alter the typical process followed by a medical staff when administering a medicine by injection.

SUMMARY OF THE INVENTION

An aspect of the present invention is therefore to provide a plunger rod, to be used to form an injection device, for example in combination with a container, this plunger rod being of simple use for the end-user, allowing the reduction of the overall length and volume of the injection device in the storage position, even when the container of the injection device is prefilled with a product, said plunger rod further comprising means for setting specific doses of the product to be injected.

An aspect of the invention is a plunger rod for an injection device comprising:
  a distal element having a proximal end and a distal end,
  a proximal element having at least one radially flexible branch, wherein the proximal element is slidingly coupled to the distal element and selectively movable in an axial direction between a restricted position of the plunger rod and an extended position of the plunger rod,
  locking means for selectively locking the distal element and the proximal element in a plurality of relative axial positions defining a plurality of intermediate positions of the plunger rod,
  wherein the locking means is movable from a locked state, in which the distal element and the proximal element are fixed with respect to each other in the axial direction, and an unlocked state, in which the distal element and the proximal element are displaceable in the axial direction with respect to each other, when the radially flexible branch is displaced radially.

For example, if the injection device the plunger rod is intended to be used with comprises a container comprising a tubular barrel, the plunger rod has a longitudinal axis: the length of the plunger rod being defined as being the distance between the distal end of the distal element and the proximal end of the proximal element, then the proximal element is movable in longitudinal translation with respect to the distal element between a restricted position of the plunger rod, in which the plunger rod has a first length L1, and an extended position of the plunger rod, in which the plunger rod has a second length L2 greater than L1.

In particular, the locking means are capable of releasably locking the proximal element with respect to the distal element in longitudinal translation in a plurality (n) of intermediate axial positions, in which the plunger rod has a length between L1 and L2.

By "slidingly coupled" is meant according to the present application that the proximal element and the distal element are linked to each other, yet with a possibility of each element to move with respect to the other along the longitudinal axis of the plunger rod, both in the distal and the proximal directions.

Another aspect of the invention is an injection device capable of delivering one or more selected dose(s) of a product contained in a container comprising a tubular barrel open at its proximal end and defining an outlet at its distal end, comprising a plunger rod as described herein said plunger rod being intended to be slidingly disposed within the tubular barrel.

The plunger rod of the invention may be combined to a container comprising a tubular barrel in order to form an injection device, in particular with a container intended to receive a product to be injected, said container comprising a tubular barrel provided at its distal end with a port intended to receive an injection needle, said product being intended to be expelled from said tubular barrel under distal displacement of a stopper movable within said tubular barrel by said plunger rod.

In particular, the plunger rod of the invention is intended to be received within the tubular barrel in order to move the stopper lodged therein at the time of injection. For example, in a storage position of the injection device, the plunger rod may be in its restricted position, thereby limiting the volume occupied by the injection device, even if the container is prefilled with a product to be injected. In addition, the plunger rod of the invention may adopt a plurality of intermediate positions allowing it to safely deliver selected doses of product, successively for example, as will appear from the description below.

In embodiments, said flexible branch extends substantially in the axial direction and includes a free proximal end that is displaceable radially inward.

In embodiments, the plunger rod further comprises one or more transversal wall(s) mounted at a proximal end of the proximal element, said one or more transversal wall(s) forming a thumb press. For example, the free proximal end of said flexible branch is provided with at least one of said transversal wall(s).

As will appear from the description below, the transversal wall(s) may form safe stopping means at the end of the injection of a selected dose of product, by coming in abutment against a proximal end of the container with which the plunger rod of the invention is combined.

In embodiments, the locking means comprises a surface on said radially flexible branch and a cooperating surface on the distal element to maintain the locking means in the locked state.

In embodiments, said distal element comprising a tubular portion capable of slidingly receiving at least part of said flexible branch, said tubular portion having an inner wall, the locking means comprise a plurality (n) of reliefs axially spaced from one another and located on one of said inner wall and said part of said flexible branch, and at least one complementary relief located on the other of said inner wall and said part of said flexible branch, each of said plurality of reliefs being capable of successively cooperating with said complementary relief, so as to maintain the locking means in the locked state and said plunger rod in one of its restricted, intermediate or extended positions.

As the two elements forming the plunger rod, in other words the distal element and the proximal element, are allowed to slide with respect to each other, at least a part of the proximal element, in particular the flexible branch, is capable of disappearing within the tubular portion of the distal element, thereby reducing the global length of the plunger rod, and thus reducing the overall length of the injection device in a storage position for example.

For example, the reliefs being selected from recesses and radial projections, said complementary relief is respectively selected from a radial projection and a recess.

In embodiments, the plunger rod further comprises guiding means for preventing rotation of said proximal element with respect to said distal element. For example, the guiding means comprises a longitudinal channel, located on one of said proximal element and distal element, and a peg attached to the other of said proximal element and distal element, said peg being slidable within the longitudinal channel. Such guiding means ensure that the plunger rod travels safely along a linear and efficient way.

In embodiments, said longitudinal channel is provided with a distal stop and with a proximal stop, said peg being constrained from moving out of the channel by said proximal and distal stops. The proximal element is therefore prevented from being separated from the distal element and the integrity of the plunger rod is ensured all along its use.

In embodiments, the tubular portion of said distal element is closed at its distal end.

In embodiments, the plunger rod is further provided with fixing means for attaching a stopper at the distal end of said distal element. For example, a screw may be present at the distal end of the distal element, said screw being capable of cooperating with a thread present on a stopper, so as to attach said stopper to the plunger rod. In embodiments, the plunger rod therefore comprises a stopper attached at the distal end of said distal element.

In embodiments, the plunger rod is dimensioned so that only said transversal wall(s) as described above extend beyond the proximal end of said tubular barrel in the proximal direction, in a before use position of the injection device, in which said tubular barrel is prefilled with said product and closed at its proximal end with a stopper, a distal end of said plunger rod facing a proximal end of said stopper, said plunger rod being in its restricted position.

In such embodiments, the plunger rod does not extend beyond the proximal end of the tubular barrel on a long distance and the injection device therefore occupies only a limited overall volume.

In embodiments, said tubular barrel is provided with an outer flange at its proximal end. Such an outer flange may form a bearing surface for the fingers of the user at the time the injection step is completed.

For example, in a ready for injection position of said injection device, said plunger rod is in one of its intermediate or extended positions, said intermediate or extended position thereby determining a specific dose of product to be delivered.

For example, a proximal end of said tubular barrel forms a stopping means for the plunger rod at the end of an injection step of a selected dose of product, when said transversal wall(s) comes in abutment against said proximal end. For example, when said proximal end is an outer flange, the transversal wall(s) may come in abutment against the outer flange, thereby securing the end of the injection of the preselected dose of product.

BRIEF DESCRIPTION OF THE DRAWINGS

The present invention will now be described in greater detail based on the following description and the appended drawings in which:

FIG. 6 is a cross section view of an embodiment of the injection device of the invention, comprising the plunger rod of FIG. 1, in its storage position, FIG. 7 is a cross section of the injection device of FIG. 6 in a ready-to-use position, with a preset selected dose of the product to be injected.

DETAILED DESCRIPTION

Figure 1:
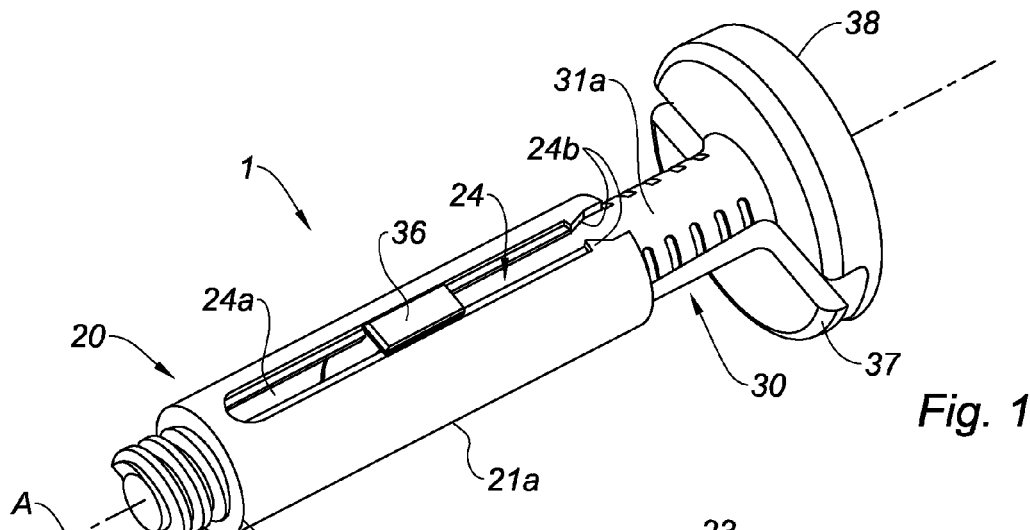
FIG. 1 is a perspective view of an embodiment of the plunger rod of the invention.

With respect to FIG. 1 is shown a plunger rod 1 of the invention, which may be used in combination with a container having a tubular barrel, in order to obtain an injection device occupying only a restricted volume, and allowing the delivery of successive doses of preset selected doses of product.

Figure 2:
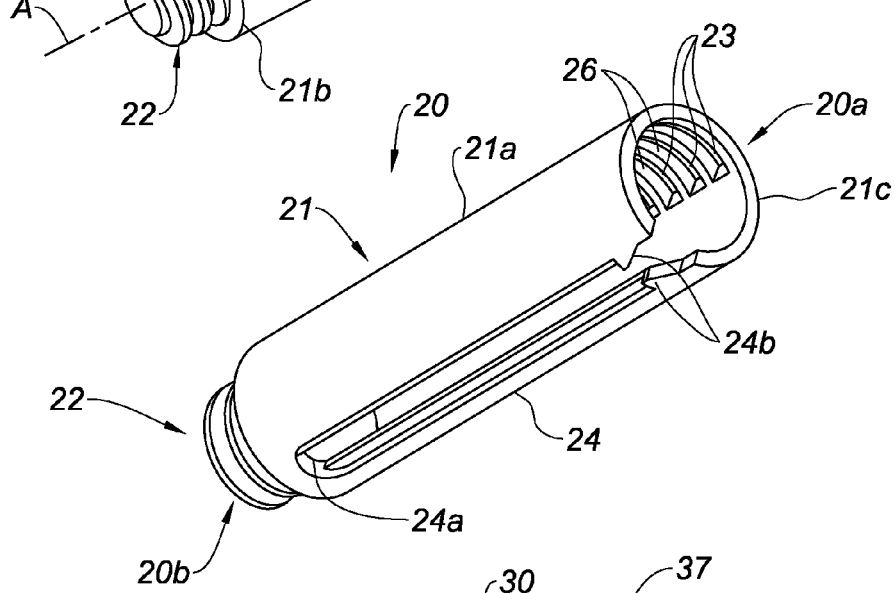
FIG. 2 is a perspective view of the distal element of the plunger rod of FIG. 1.
Figure 3:
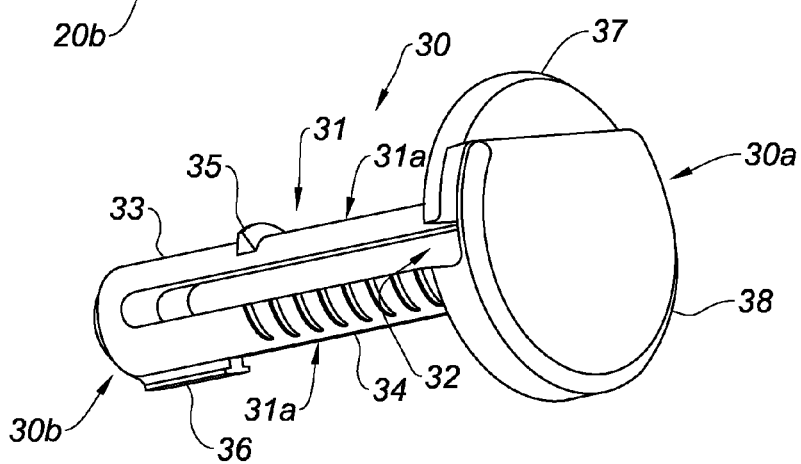
FIG. 3 is a perspective view of the proximal element of the plunger rod of FIG. 3.

With reference to FIGS. 1-3, the plunger rod 1 of the invention has a longitudinal axis A and comprises a distal element 20 having a proximal end 20a and a distal end 20b, and a proximal element 30, having a proximal end 30a and a distal end 30b.

With reference to FIG. 2, the distal element 20 has the global shape of a tube 21 comprising a tubular portion 21a open at its proximal end and closed at its distal end by a transversal wall 21b. On the example shown, the transversal wall 21b is further provided with a screw 22 extending in the distal direction: as will appear later from the description, the screw 22 may be used for attaching thereon a stopper. In embodiments not shown, no connection means like the screw 22 or a plug are provided at the distal end of the distal element.

Still with reference to FIG. 2, the inner wall 21c of the tubular portion 21a of the distal element 20 is provided with a plurality of reliefs under the form of parallel recesses 23 axially spaced from one another and distributed along the length of said inner wall 21c. As appears from FIG. 4A, ten parallel recesses 23 are present on the inner wall 21c. In the example shown, these recesses 23 are grooved through the whole thickness of the wall 21c: in embodiments not shown, the recesses 23 may not go through the whole thickness of the inner wall 21c. The recesses 23 are separated from each other by arched walls 26. The tubular portion 21a further comprises a longitudinal channel 24, closed at its distal end by a distal stop 24a and provided at its proximal end with two circumferential dots 24b restricting the width of the longitudinal channel 24 at this location, and forming a proximal stop.

With reference to FIG. 3, the proximal element 30 has the global shape of a cylinder 31 comprising a cylindrical portion 31a provided with a longitudinal slot 32: the longitudinal slot 32 is closed at the distal end 30b of the cylindrical portion 31a and open at the proximal end 30a of the cylindrical portion 31a. As such, the longitudinal slot 32 therefore separates the cylindrical portion 31a in two branches, a first branch 33 and a second branch 34, which face each other, the first branch 33 being radially flexible. On the example shown, the first branch 33 is further provided on its outer wall with a relief which is complementary with the recesses 23 of the distal element 20, this complementary relief having here the form of a radial projection 35. As appears more clearly from FIGS. 5A and 5B, the radial projection 35 has a sloped proximal face 35a. On the outer wall of the second branch 34, opposite the first branch 33, is provided a peg 36, said peg being capable of being lodged within the longitudinal channel 24 of the distal element 20, in which it is allowed to slide.

Still with reference to FIG. 3, the first branch 33 is further provided at its proximal end with a transversal wall 37 and the second branch 34 is also provided at its proximal end with a transversal wall 38. As will appear from the description below, the two transversal walls (37, 38) may form a thumb press surface for the user at the time of injection.

Figure 4A:
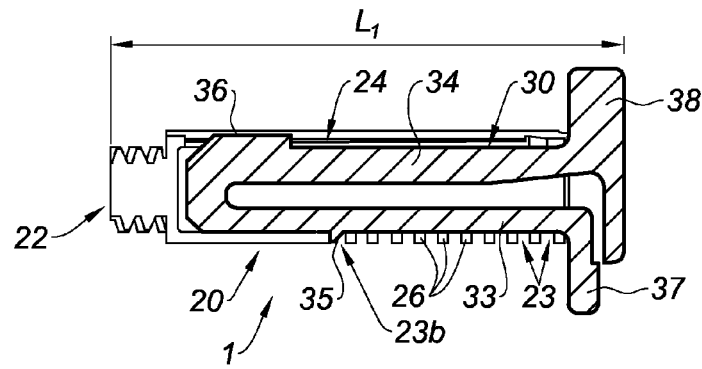
FIG. 4A is a cross section view of the plunger rod of FIG. 1 in the retracted position.
Figure 4B:
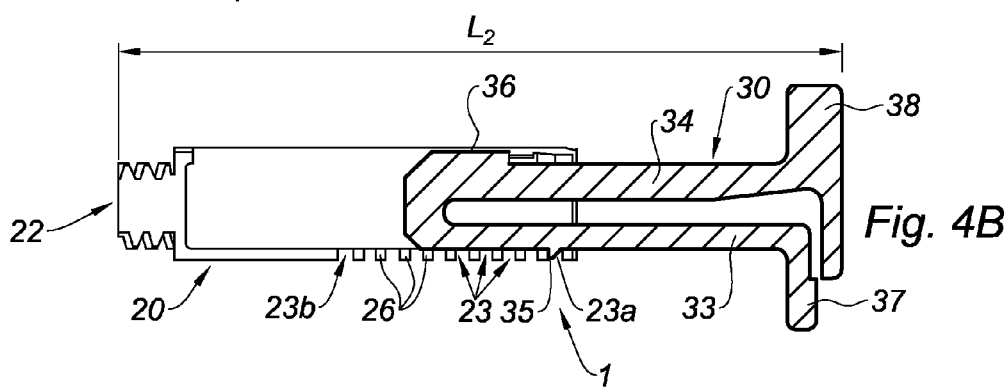
FIG. 4B is a cross section view of the plunger rod of FIG. 1 in the extended position.

With reference to FIGS. 1 and 4A and 4B, in the use position of the plunger rod 1 of the invention, the proximal element 30 and the distal element 20 are coupled to each other and at least part of the proximal element 30, in particular part of its cylindrical portion 31a and the flexible branch 33, is received within part of the distal element 20, in particular within part of the tubular portion 21a, in sliding translation along the longitudinal axis A of the plunger rod 1. As appears from these Figures, in the use position of the plunger rod 1, the peg 36 is received within the longitudinal channel 24, with no possibility of escaping said longitudinal channel 24: indeed, the longitudinal channel 24 is closed at one end by its distal stop 24a; at the other end, the peg 36 is prevented from further proximal movement when it comes in abutment against the circumferential dots 24b forming a proximal stop. The proximal element 30 is therefore coupled to the distal element 20 with limited movement in the proximal and distal directions. As such, the overall length of the plunger rod 1 of the invention may vary between two values, L1 and L2, depending on two extreme positions of the proximal element 30 with respect to the distal element 20, as shown on FIGS. 4A and 4B.

With reference to FIG. 4A, the plunger rod 1 is shown in its restricted position, where the radial projection 35 is engaged in the most distal recess 23a of the plurality of recesses 23. In this position, the length of the plunger rod 1, which is defined by the distance between the distal end 20b of the distal element 20, i.e. the distal end of the screw 22 on the example shown, and the proximal end 30a of the proximal element 30, i.e. the proximal end of the transversal wall 38 of the second branch 34 on the example shown, is L1.

With reference to FIG. 4B, the plunger rod 1 is shown in its extended position, where the radial projection 35 is engaged in the most proximal recess 23b of the plurality of recesses 23. In this position, the length of the plunger rod 1, as defined above is L2, as shown on the FIG. 4B.

As appears from FIGS. 4A and 4B, the length of the plunger rod 1 of the invention may vary between a first length L1, in which the plunger rod 1 is in a restricted position, and a second length L2, in which the plunger rod 1 is in an extended position, where L2 is greater than L1.

In these two respective positions of the plunger rod 1, the proximal element 30 is fixed with respect to the distal element 20 in the axial direction, by means of the radial projection 35 being engaged respectively in most distal recess 23b or most proximal recess 23a. The radial projection 35 and the most distal recess 23b and the most proximal recess 23a form locking means which are therefore in the locked state. These locking means are releasable and are movable in an unlocked state, when the flexible branch 33 is displaced radially, as shown on FIGS. 5A and 5B.

Figure 5A:
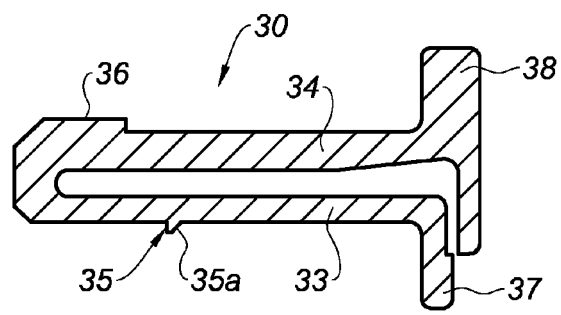
FIG. 5A is a cross section view of the proximal element of the plunger rod of FIG. 1, in the rest state of the radially flexible branches.
Figure 5B:
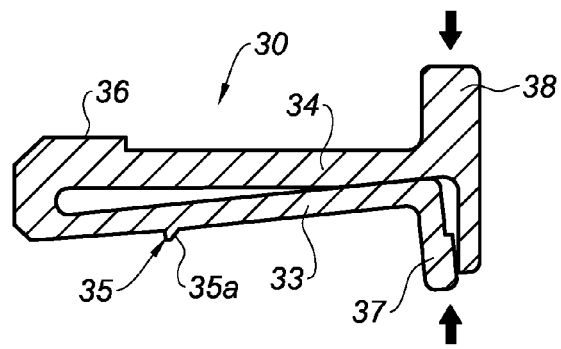
FIG. 5B is a cross section view of the proximal element of the plunger rod of FIG. 1, in the stressed state of the radially flexible branches.

With reference to FIGS. 5A and 5B is shown the proximal element 30 of the plunger rod 1 of FIG. 1, the radially flexible first branch 33 being respectively in its rest state and in its radially deflected state. The rest state of the first branch 33 corresponds to a state where the first branch 33 is not submitted to any stress and its free proximal end is not displaced radially inward: this state is also shown on FIGS. 4A and 4B, in combination with the distal element 20: in this state, the radial projection 35 is engaged in one of the recesses 23. When the first branch 33, in particular its free proximal end, is submitted to a radially inward directed force, as shown on FIG. 5B, via for example a user pushing radially inward on the transversal wall 37, said first branch 33 deflects inwardly radially, and the radial projection 35 gets disengaged from the recess 23 it was engaged in. The distal element 20 and the proximal element 30 become therefore displaceable in the axial direction with respect to each other. The user may then move the proximal element 30 in translation with respect to the distal element 20, either in the distal or in the proximal direction, depending on the starting position of the plunger rod 1 (restricted or extended).

In the same manner as just described above, the plunger rod 1 of the invention may further adopt a plurality of intermediate positions, in which the plunger rod 1 has a length comprised between L1 and L2: these intermediate positions correspond to the case where the radial projection 35 is engaged in one of the recesses 23 located between the most distal recess 23b and the most proximal recess 23a. On the example shown on the Figures, ten recesses 23 are present, including the most distal recess 23b and the most proximal recess 23a. As such, in addition to its restricted position and to its extended position, the plunger rod 1 may adopt eight different intermediate positions, each intermediate position corresponding to the engagement of the radial projection 35 with one of the eight recesses 23 located between the most distal recess 23b and the most proximal recess 23a.

As seen above, the radial projection 35 located on the radially flexible first branch 33 and the recesses 23 of the tubular portion 21a form releasable locking means of the proximal element 30 with respect to the distal element 20 in the axial direction: moreover, as appears from FIGS. 4A and 4B, for each intermediate position of the plunger rod 1, the length of the plunger rod 1 will be between L1 and L2.

Figure 8:
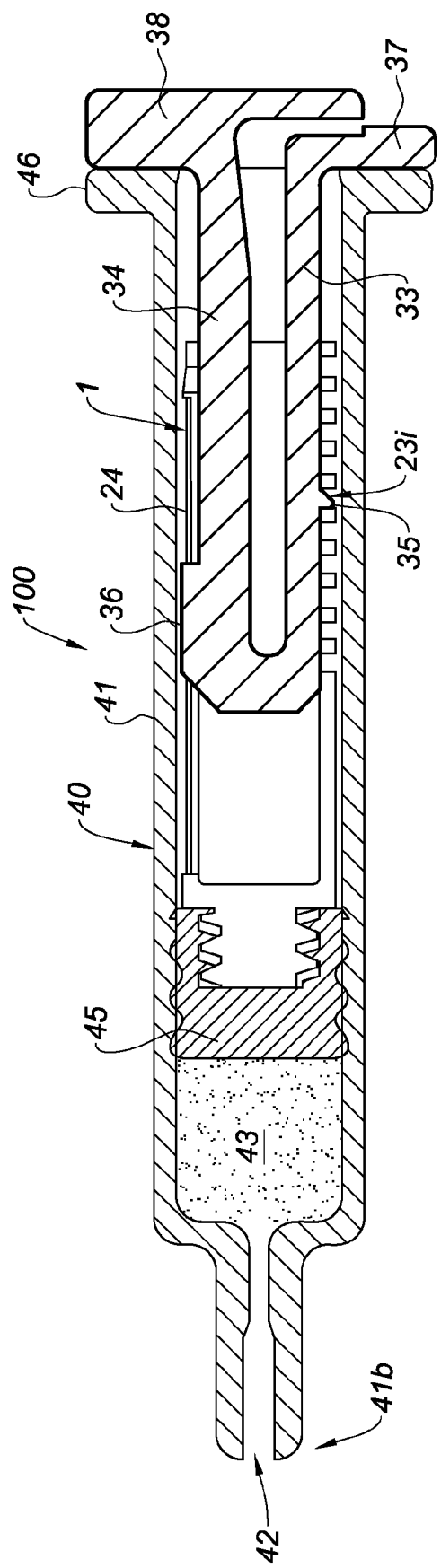
FIG. 8 is a cross section view of the injection device of FIG. 7 at the end of the injection of the preset selected dose of product.

With reference to FIGS. 6-8, in which the plunger rod 1 of FIGS. 1-5b is combined to a container in order to form an injection device, it will now be explained how the plunger rod 1 of the invention allows the delivery of successive selected doses of a product to be injected.

With reference to FIG. 6, an injection device 100 of the present invention, comprising the plunger rod 1 of FIGS. 1-5B is shown in a storage position.

The injection device 1 comprises a container 40 comprising a tubular barrel 41 open at its proximal end and substantially closed at its distal end 41b, except for an outlet 42 for the passage of the product to be expelled. In the example shown, the container 40 is filled with a product 43 to be injected. The container 40 is further provided at its proximal end with an outer flange 46. In this storage position of the injection device 100, the distal end 41b of the tubular barrel 41 is provided with a cap 44 for preventing the product 43 to leak out of the container 40. The tubular barrel 41 is further closed at its proximal end with a stopper 45 also preventing the product 43 from leaking out of the container 40. In the storage position of the injection device as shown on FIG. 6, the plunger rod 1 is in its restricted position, with the radial projection 35 engaged in the most distal recess 23b. Moreover the screw 22 is screwed within the stopper 45, thereby attaching the plunger rod 1 to the stopper 45.

As appears from FIG. 6, in these respective positions of the plunger rod 1 and of the injection device 100, in other words, in the restricted position of the plunger rod 1 and in the prefilled condition of the injection device 100 in his storage position, the plunger rod 1 extends beyond the proximal end of the container 40, i.e. beyond the outer flange 46 in the example shown, only by the thickness of the transversal walls (37, 38) of the first and second branches (33, 34). The plunger rod 1 is dimensioned so that only the transversal walls (37, 38) extend beyond the proximal end of the tubular barrel in the proximal direction, in the before use position of the injection device 100. The overall length of the injection device 100 in his storage position is therefore not dramatically increased by the presence of the plunger rod 1 of the invention, in particular regarding the length of standard injection devices having traditional plunger rods. As such, the injection device 100 in his storage position occupies a limited volume and its packaging and storage is facilitated.

When the user wishes to proceed to the injection step, in particular to the injection step of a predetermined dose of product, he grasps the transversal walls (37, 38) of the proximal element 30 and he pulls on said proximal element 30 in the proximal direction. For doing this, he may either simply pull on the two transversal walls (37, 38) without exerting any radial inward force on these two transversal walls (37, 38) as the sloped proximal face 35a of the radial projection 35, combined to the flexible nature of the first branch 33, allows the radial projection 35 to overcome the adjacent arched wall 26, or he may exert radial inward pressure on the transversal wall 37 provided at the free proximal end of the flexible branch 33, thereby radially displacing said free proximal end of flexible branch 33 so as to maintain the locking means in their unlocked state, in other words to maintain the radial projection 35 disengaged from the recesses 23, during the proximal movement of the proximal element 30. The user pulls on the proximal element 30 until the radial projection 35 reaches the recess 23 corresponding to the selected dose the user wants to inject.

As an example, with reference to FIG. 7, the user has pulled the proximal element 30 in the proximal direction until the radial projection 35 reaches the recess 23i, corresponding to the fifth recess 23 starting from most proximal recess 23a as first recess 23. Alternatively, the user could have chosen any one of the second to the fourth, or of the sixth to the ninth recesses 23. The choice of a specific recess by the user is dependent on the volume of the dose of product he wishes to inject. In addition, in case the user makes a mistake and engages the radial projection 35 in the wrong recess 23 in the first place, he may simply disengage the radial projection 35 by exerting a radial pressure on the transversal wall 37 of the free proximal end of flexible branch 33 as shown on FIGS. 5A and 5B, and move again the proximal element 30 with respect to the distal element 20, either in the distal or in the proximal direction, in order to reach the correct recess 23 and therefore the correct volume of dose of product to be injected.

When the user has set the selected dose and the locking means are in their locked state by means of the radial projection 35 being engaged in the adequate recess 23, the user then removes the cap 44 and if necessary, attaches a needle (not shown) at the proximal end of the container 40. The plunger rod 1 is then in a ready-to-use position, as the proximal element 30 is fixed in the axial direction with respect to the distal element 20. The user then applies a distal force on the transversal walls (37, 38) of the proximal element 30 forming a thumb press, thereby moving the plunger rod 1, and thus the stopper 45, in the distal direction with respect to the tubular barrel 41, causing at least part of the product 43 to be expelled from the container 40 through the outlet 42 and realizing the injection step.

At the end of the injection of the selected dose of product 43, the transversal walls (37, 38) of the proximal element 30 of the plunger rod 1 come in abutment against the outer flange 46 of the container 40, thereby stopping the movement of the plunger rod 1, and thus of the stopper 45, with respect to the tubular barrel 41 as shown on FIG. 8. The user is thus certain to have injected only the predetermined dose of product 43.

As shown on FIG. 8, some of the product 43 may still be present in the container 40. If desired, the user may then deliver a second selected dose of product 43 by disengaging the radial projection 35 from the recess 23i as explained before, and repeat the step already described for FIG. 7, i.e. pulling the proximal element 30 in the proximal direction and this time engaging the radial projection 35 in one of the first to fourth recesses 23, so as to determine a subsequent selected dose of product to be injected.

The plurality of recesses 23 and the radial projection 35 combined with the flexible nature of the first branch 33 therefore form releasably locking means, in other words locking means capable of being moved from a locked state to an unlocked state, for successively fixing the proximal element 30 with respect to the distal element 20 in the axial direction, thereby providing the plunger rod 1 with a plurality of intermediate positions, in which the length of the plunger rod 1 is comprised between the smallest length L1 of the plunger rod 1, corresponding to its restricted position, and the biggest length L2 of the plunger rod 1, corresponding to its extended position. This plurality of intermediate positions of the plunger rod 1 determines setting means for setting a selected dose of product to be injected when the plunger rod 1 is combined with a container in order to form the injection device.

In embodiments not shown, the recesses could be located on the flexible branch of the proximal element, and the radial projection could be located on the inner wall of the tubular portion of the distal element. Alternatively or in combination, the longitudinal channel could be located on the proximal element and the peg could be attached to the distal element.

The plunger rod of the invention allows obtaining injection devices capable of delivering successive selected doses of product while occupying a limited volume in their storage position, even when said injection devices are prefilled with the product to be injected.

The invention claimed is:

1. A plunger rod for an injection device comprising:
a distal element having a proximal end and a distal end,
a proximal element having at least one radially flexible branch, wherein the proximal element is slidingly coupled to the distal element and selectively movable in an axial direction between a restricted position of the plunger rod and an extended position of the plunger rod, and wherein said at least one flexible branch extends in the axial direction and includes a free proximal end that is displaceable radially inward,
at least one transversal wall mounted at a proximal end of the proximal element, said at least one transversal wall forming a thumb press, and
a lock for selectively locking the distal element and the proximal element in a plurality of relative axial positions defining a plurality of intermediate positions of the plunger rod,
wherein the lock is movable from a locked state, in which the distal element and the proximal element are fixed with respect to each other in the axial direction, and an unlocked state, in which the distal element and the proximal element are displaceable in the axial direction with respect to each other, when the at least one radially flexible branch is displaced radially.

2. The plunger rod according to claim 1, wherein the free proximal end of said at least one radially flexible branch is provided with at least one said transversal wall.

3. The plunger rod according to claim 1, wherein the lock comprises a surface on said at least one radially flexible branch and a cooperating surface on the distal element to maintain the lock in the locked state.

4. The plunger rod according to claim 1, wherein said distal element comprises a tubular portion capable of slidingly receiving at least part of said at least one radially flexible branch, said tubular portion having an inner wall, the lock comprising a plurality of reliefs axially spaced from one another and located on one of said inner wall and said part of said at least one radially flexible branch, and at least one complementary relief located on the other of said inner wall and said part of said at least one radially flexible branch, each relief of said plurality of reliefs being capable of successively cooperating with said complementary relief, so as to maintain the lock in the locked state and said plunger rod in one of the fixed, intermediate or displaceable positions.

5. The plunger rod according to claim 4, wherein each relief is a recess or a radial projection, and said complementary relief is the other of the radial projection and the recess.

6. The plunger rod according to claim 1, wherein the plunger rod further comprises a guide for preventing rotation of said proximal element with respect to said distal element.

7. The plunger rod according to claim 6, wherein the guide comprises a longitudinal channel, located on one of said proximal element and distal element, and a peg attached to the other of said proximal element and distal element, said peg being slidable within the longitudinal channel.

8. The plunger rod according to claim 7, wherein said longitudinal channel is provided with a distal stop and a proximal stop, said peg being constrained from moving out of the channel by said proximal and distal stops.

9. The plunger rod according to claim 4, wherein the tubular portion of said distal element is closed at the distal end.

10. The plunger rod according to claim 1, further comprising a fixing element for attaching a stopper at the distal end of said distal element.

11. The plunger rod according to claim 10, further comprising a stopper attached at the distal end of said distal element.

12. An injection device capable of delivering one or more selected dose(s) of a product contained in a container comprising a tubular barrel open at a proximal end and defining an outlet at a distal end, the injection device comprising:
a plunger rod having:
a distal element having a proximal end and a distal end,
a proximal element having at least one radially flexible branch, wherein the proximal element is slidingly coupled to the distal element and selectively movable in an axial direction between a restricted position of the plunger rod and an extended position of the plunger rod, and wherein said at least one flexible branch extends in the axial direction and includes a free proximal end that is displaceable radially inward, and
a lock for selectively locking the distal element and the proximal element in a plurality of relative axial positions defining a plurality of intermediate positions of the plunger rod,
wherein the lock is movable from a locked state, in which the distal element and the proximal element are fixed with respect to each other in the axial direction, and an unlocked state, in which the distal element and the proximal element are displaceable in the axial direction with respect to each other, when the at least one radially flexible branch is displaced radially,
wherein said plunger rod is intended to be slidingly disposed within the tubular barrel.

13. The injection device according to claim 12, wherein said plunger rod further comprises at least one transversal wall mounted at a proximal end of the proximal element, said at least one transversal wall forming a thumb press, and wherein said plunger is dimensioned so that only said at least one transversal wall extends beyond the proximal end of said tubular barrel in a proximal direction, in a before use position of the injection device, in which said tubular barrel is prefilled with said product and closed at the proximal end with a stopper, a distal end of said plunger rod facing a proximal end of said stopper, said plunger rod being in a restricted position.

14. The injection device according to claim 12, wherein said tubular barrel is provided with an outer flange at a proximal end.

* * * * *